(12) United States Patent
Outtrup et al.

(10) Patent No.: US 6,280,984 B1
(45) Date of Patent: Aug. 28, 2001

(54) DNA CONSTRUCTS AND METHODS OF PRODUCING CELLULYTIC ENZYMES

(75) Inventors: Helle Outtrup, Bellerup; Claus Dambmann, Søborg; Arne Agerlin Olsen, Virum; Henrik Bisgård-Frantzen, Lyngby; Martin Schülein; Per Linaa Jorgensen, both of Copenhagen; Mads E. Bjoernvad, Frederiksberg, all of (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/226,529

(22) Filed: Jan. 7, 1999

Related U.S. Application Data

(60) Division of application No. 08/870,180, filed on Jun. 6, 1997, now Pat. No. 5,945,327, which is a continuation-in-part of application No. 08/713,298, filed on Sep. 13, 1996, now Pat. No. 5,922,586, which is a continuation-in-part of application No. 08/343,600, filed on Nov. 30, 1994, now Pat. No. 5,741,693, and a continuation-in-part of application No. PCT/DK93/00218, filed on Jul. 2, 1993.

(30) Foreign Application Priority Data

Jul. 2, 1992 (DK) .................................................. 870/92

(51) Int. Cl.⁷ ............................... C12P 19/04; C12N 9/42
(52) U.S. Cl. ............................................ 435/137; 435/204
(58) Field of Search .................................. 435/209, 137, 435/101

(56) References Cited

U.S. PATENT DOCUMENTS

| | | | |
|---|---|---|---|
| 4,904,599 | * 2/1990 | Ozaki et al. | 435/252.22 |
| 4,945,053 | * 7/1990 | Ito et al. | 435/209 |
| 5,231,022 | 7/1993 | Saito et al. | 435/209 |

FOREIGN PATENT DOCUMENTS

| | | |
|---|---|---|
| 0 270 974 A2 | 6/1988 | (EP) . |
| 0 339 550 A2 | 11/1989 | (EP) . |
| 0 468 464 A2 | 1/1992 | (EP) . |
| 1-101884 | 4/1989 | (JP) . |
| WO 91/10732 | 7/1991 | (WO) . |
| WO 94/01532 | 1/1994 | (WO) . |
| WO 96/34092 | 10/1996 | (WO) . |
| WO 96/34108 | 10/1996 | (WO) . |

OTHER PUBLICATIONS

Nakamura, A., et al. (1991) J. Biol. Chem. 266(3), 1579–1583.*
Yoshimatsu, T., et al. (1990) J. Gen. Microbiol. 136, 1973–1979.*
Shikata, S., et al. (1990) Agric. Biol. Chem. 54(1), 91–96.*
Sanchez, Torres J. GenBank #Z33876, submitted May 20, 1994.
Fukmori, F. et al., J. Bacteriol. 168(2) :479–485 (1986).
Sanchez–Torres et al., Appl. Microbiol. Biotechnol., vol. 46, pp. 149–155 (1996).
Abstract of Japanese Patent 1–91772 (A) (1983).
Abstract of Japanese Patent 1–112982 (A) (1989).

* cited by examiner

*Primary Examiner*—Charles L. Patterson, Jr.
(74) *Attorney, Agent, or Firm*—Elias J. Lambiris; Jason I. Garbell

(57) ABSTRACT

An isolated nucleic acid constructs encoding cellulytic enzymes derived from a strain of *Bacillus agaradherens*, recombinant vectors and host cells comprising such constructs, and methods for obtaining cellulytic enzymes.

15 Claims, No Drawings

DNA CONSTRUCTS AND METHODS OF PRODUCING CELLULYTIC ENZYMES

CROSS-REFERENCE TO RELATED APPLICATIONS

This application is a divisional of U.S. application Ser. No. 08/870,180 filed Jun. 6, 1997, now U.S. Pat. No. 5,945,327, which is a continuation-in-part of U.S. application Ser. No. 08/713,298 filed Sep. 13, 1996 now U.S. Pat. No. 5,922,586, which is a continuation-in-part of U.S. application Ser. No. 08/343,600 filed Nov. 30, 1994, now U.S. Pat. No. 5,741,693, and PCT/DK93/00218 filed Jul. 2, 1993, and claims priority under 35 U.S.C. 119 of Danish application 870/92 filed Jul. 2, 1992, the contents of which are fully incorporated herein by reference.

FIELD OF THE INVENTION

The present invention relates to isolated nucleic acid sequences and constructs encoding cellulytic enzymes derived from a strain of Bacillus, recombinant expression vectors and host cells comprising such constructs, and methods for obtaining cellulytic enzymes.

BACKGROUND OF THE INVENTION

PCT publication WO 94/01532 describes a new species of alkalophilic Bacillus, initially named Bacillus sp. AC13, as well as proteases, xylanases and cellulases obtainable therefrom. A sample of the strain was deposited as NCIMB 40482. WO 94/01532 also describes methods for the production of these enzymes by cultivation of a strain of Bacillus sp. AC13. However, WO 94/01532 does not describe nucleic acid constructs comprising a nucleic acid sequence encoding cellulytic enzymes derived from a strain Bacillus sp. AC13, or methods of producing these cellulytic enzymes by recombinant DNA technology.

The same new species as described in WO 94/01532 has been described by Nielsen et al. (1995) Microbiology 141:1745–1761, with the now established name, *Bacillus agaradhierens*. A sample of the strain has been deposited as DSM 8721. Nielsen et al. (1995) supra, however, do not describe nucleic acid sequences or constructs encoding cellulytic enzymes derived from a strain *Bacillus agaradhierens*, or methods of producing these cellulytic enzymes by recombinant DNA technology.

SUMMARY OF THE INVENTION

The invention features an isolated DNA sequence derived from Bacillus encoding a cellulytic enzyme, thereby making it possible to prepare a mono-component enzyme preparation.

Accordingly, in one aspect, the invention provides an isolated DNA sequence derived from *Bacillus agaradhierens* encoding a polypeptide having cellulytic enzyme activity. In a specific embodiment, the isolated DNA sequence is the sequence of SEQ ID NO:1. In another related embodiment, the isolated DNA sequence is a DNA sequence encoding a cellulytic enzyme having more than 98% homology to the cellulytic enzyme encoded by the DNA sequence of SEQ ID NO:1. Included in the invention is an isolated DNA sequence complementary to SEQ ID NO:1, and a fragment of the sequence of SEQ ID NO:1 (or its complementary sequence) that is at least 15 base pairs in length that selectively hybridizes under stringent conditions to DNA sequences encoding the cellulytic enzyme of SEQ ID NO:1. In still further embodiments, the DNA sequence is isolated from a Bacillus strain identified by the deposit accession number DSM 8721 or NCIMB 40482.

In further aspects, the invention provides a DNA construct having the DNA sequence of SEQ ID NO:1, an expression vector harboring the DNA construct of the invention, a cell having the DNA construct or expression vector of the invention, as well as a method of producing a cellulytic enzyme by culturing the cell of the invention under conditions permitting the production of the cellulytic enzyme, and recovering the cellulytic enzyme from the culture.

In another aspect, the invention features an isolated polypeptide encoded by SEQ ID NO:1 and having cellulytic activity. The invention includes an isolated polypeptide having the amino acid sequence of SEQ ID NO:2, or a polypeptide having an amino acid sequence with at least 80%, 90%, or 95% identity with the amino acid sequence of SEQ ID NO:2.

The invention further features an enzyme preparation comprising the cellulytic enzyme encoded by the DNA sequence of SEQ ID NO:1.

DETAILED DISCLOSURE OF THE INVENTION

Before the methods and compositions of the present invention are described and disclosed it is to be understood that this invention is not limited to the particular methods and compositions described as such may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "an" and "the" include plural referents unless the context clearly dictates otherwise. Thus, for example, reference to "a DNA sequence" includes a plurality of DNA sequences and different types of DNA sequences.

Unless defined otherwise all technical and scientific terms used herein have the same meaning as commonly understood by one of ordinary skill in the art to which this invention belongs. Although any materials or methods similar or equivalent to those described herein can be used in the practice or testing of the present invention, the preferred methods and materials are now described. All publications mentioned herein are incorporated herein by reference for the purpose of describing and disclosing the particular information for which the publication was cited. The publications discussed above are provided solely for their disclosure prior to the filing date of the present application. Nothing herein is to be construed as an admission that the inventor is not entitled to antedate such disclosure by virtue of prior invention.

Isolated DNA Sequences and DNA Constructs

The present invention provides an isolated DNA sequence and a construct comprising the DNA sequence encoding a cellulytic enzyme. The DNA sequence of the invention includes (a) the DNA sequence of SEQ ID NO:1, (b) a DNA sequence encoding a polypeptide having more than 98% homology with the cellulytic enzyme encoded by SEQ ID NO:1, (c) a sequence complementary to SEQ ID NO:1, and (d) a fragment of the sequence of (a), (b), or (c) that is at least 15 base pairs in length that selectively hybridizes under stringent conditions to DNA sequences encoding the cellulytic enzyme of SEQ ID NO:1.

As defined herein the term "DNA construct" is intended to indicate any nucleic acid molecule of cDNA, genomic DNA, synthetic DNA or RNA origin. The term "construct" is intended to indicate a nucleic acid segment which may be single- or double-stranded, and which may be based on a complete or partial naturally occurring nucleotide sequence encoding a cellulytic enzyme of interest. It is understood that such nucleotide sequences include intentionally manipulated nucleotide sequences, e.g., subjected to site-directed mutagenesis, and sequences that are degenerate as a result of the genetic code. All degenerate nucleotide sequences are included in the invention so long as the cellulytic enzyme encoded by the nucleotide sequence is functionally unchanged. The construct may optionally contain other nucleic acid segments.

The DNA construct of the invention preferably is of microbial origin, preferably derived from a strain of Bacillus. In its most preferred embodiments, the DNA construct of the invention is derived from a strain of the new alkalophilic species *Bacillus agaradhierens,* formerly referred to as Bacillus AC13.

The DNA construct of the invention encoding the cellulytic enzyme may suitably be of genomic or cDNA origin, for instance obtained by preparing a genomic or cDNA library and screening for DNA sequences coding for all or part of the cellulytic enzyme by hybridization using synthetic oligonucleotide probes in accordance with standard techniques (cf. e.g. Sambrook et al. (1989) *Molecular Cloning. A Laboratory Manual*, Cold Spring Harbor, N.Y.).

The nucleic acid construct of the invention encoding the cellulytic enzyme may also be prepared synthetically by established standard methods, e.g. the phosphoamidite method described by Beaucage and Caruthers (1981) Tetrahedron Letters 22:1859–1869, or the method described by Matthes et al. (1984) EMBO J. 3:801–805. According to the phosphoamidite method, oligonucleotides are synthesized, e.g. in an automatic DNA synthesizer, purified, annealed, ligated and cloned in suitable vectors.

The nucleic acid construct may also be prepared by polymerase chain reaction using specific primers, for instance as described in U.S. Pat. No. 4,683,202 or by Saiki et al. (1988) Science 239:487–491.

Furthermore, the nucleic acid construct may be of mixed synthetic and genomic DNA, mixed synthetic and cDNA, or mixed genomic and cDNA origin prepared by ligating fragments of synthetic, genomic or cDNA origin (as appropriate), the fragments corresponding to various parts of the entire nucleic acid construct, in accordance with standard techniques.

The present invention also relates to polynucleotides which are capable of hybridizing under high stringency conditions with an oligonucleotide probe which hybridizes under the same conditions with the nucleic acid sequence set forth in SEQ ID NO:1 or its complementary strand (Sambrook et al. (1989) Molecular Cloning, A Laboratory Manual, 2d edition, Cold Spring Harbor, N.Y.). Hybridization indicates that the analogous nucleic acid sequence hybridizes to the oligonucleotide probe corresponding to the polypeptide encoding part of the nucleic acid sequence of SEQ ID NO:1, under low to high stringency conditions (for example, prehybridization and hybridization at 42° C. in 5×SSPE, 0.3% SDS, 200 mg/ml sheared and denatured salmon sperm DNA, and either 50, 35 or 25% formamide for high, medium and low stringencies, respectively), following standard Southern blotting procedures.

SEQ ID NO:1 may be used to identify and clone DNA encoding a cellulytic enzyme from other strains of different genera or species according to methods well known in the art. Thus, genomic or cDNA library prepared from such other organisms may be screened for DNA which hybridizes with SEQ ID NO:1 and encodes a cellulytic enzyme. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify clones or DNA which is homologous with SEQ ID NO:1, the carrier material is used in a Southern blot in which the carrier material is finally washed three times for 30 minutes each using 2×SSC, 0.2% SDS at preferably not higher than 50° C., more preferably not higher than 55° C., more preferably not higher than 60° C., more preferably not higher than 65° C., even more preferably not higher than 70° C., especially not higher than 75° C. Molecules to which the oligonucleotide probe hybridizes under these conditions are detected using a X-ray film.

An analogous DNA sequence may preferably be isolated from a strain of Bacillus, preferably a strain of *Bacillus agaradhierens,* on the basis of the DNA sequence presented as SEQ ID NO:1, or any fragment thereof, e.g. using the procedures described herein, and thus, e.g. be an allelic or species variant of the DNA sequence comprising the DNA sequence presented herein.

Alternatively, the analogous sequence may be constructed on the basis of the DNA sequence presented as SEQ ID NO:1, or any fragment thereof, e.g. by introduction of nucleotide substitutions which do not give rise to another amino acid sequence of the cellulytic enzyme encoded by the DNA sequence, but which corresponds to the codon usage of the host organism intended for production of the enzyme, or by introduction of nucleotide substitutions which may give rise to a different amino acid sequence.

When carrying out nucleotide substitutions, amino acid changes are preferably of a minor nature, that is conservative amino acid substitutions that do not significantly affect the folding or activity of the protein, small deletions, typically of one to about 30 amino acids; small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain. Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine). For a general description of nucleotide substitution, see e.g. Ford et al. (1991) Protein Expression and Purification 2:95–107.

It will be apparent to persons skilled in the art that such substitutions can be made outside the regions critical to the function of the molecule and still result in an active cellulytic enzyme. Amino acids essential to the activity of the cellulase encoded by the DNA construct of the invention, and therefore preferably not subject to substitution, may be identified according to procedures known in the art, such as site-directed mutagenesis or alanine-scanning mutagenesis (cf. e.g. Cunningham and Wells (1989) Science 244:1081–1085). In the latter technique mutations are introduced at every residue in the molecule, and the resultant mutant molecules are tested for biological (i.e. proteolytic) activity to identify amino acid residues that are critical to the activity of the molecule. Sites of substrate-enzyme interaction can also be determined by analysis of crystal structure as determined by such techniques as nuclear magnetic resonance analysis, crystallography or photoaffinity labelling (cf. e.g. de Vos et al. (1992) Science 255:306–312; Smith et al. (1992) J. Mol. Biol. 224:899–904; Wlodaver et al. (1992) FEBS Lett. 309:59–64).

Typically, the analogous DNA sequence is highly homologous to the DNA sequence, such is more than 98% homologous to the DNA sequence presented as SEQ ID NO:1 encoding a cellulytic enzyme, preferably at least 99% homologous to said DNA sequence.

The degree of homology referred to above is determined as the degree of identity between the two sequences indicating a derivation of the first sequence from the second. The degree of identity between two nucleic acid sequences may be determined by means of computer programs known in the art such as GAP provided in the GCG program package (Needleman and Wunsch (1970) Journal of Molecular Biology 48:443–453). For purposes of determining the degree of identity between two nucleic acid sequences for the present invention, GAP is used with the following settings: GAP creation penalty of 5.0 and GAP extension penalty of 0.3.

The DNA sequence encoding the cellulytic enzyme may be isolated by conventional methods. The techniques used to isolate or clone a nucleic acid sequence encoding a polypeptide are known in the art and include isolation from genomic DNA, preparation from cDNA, or a combination thereof. The cloning of the nucleic sequences of the present invention from such genomic DNA can be effected, e.g., by using the well known polymerase chain reaction (PCR). See, e.g., Innis et al. (1990) A Guide to Methods and Application, Academic Press, New York. The nucleic acid sequence may be cloned from a strain of the *Bacillus agaradhierens*, e.g. the strain DSM 8721 or the strain NCIMB 40482, producing the polypeptide, or another or related organism and thus, for example, may be an allelic or species variant of the polypeptide encoding region of the nucleic acid sequence.

The term "isolated" nucleic acid sequence as used herein refers to a nucleic acid sequence which is essentially free of other nucleci acid sequences, e.g., at least about 20% pure, preferably at least about 40% pure, more preferably about 60% pure, even more preferably about 80% pure, most preferably about 90% pure, and even most preferably about 95% pure, as determined by agarose gel electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

Microbial Sources

The DNA construct of the invention preferably is of microbial origin, preferably derived from a strain of Bacillus. In a more preferred embodiment, the DNA construct of the invention is derived from a strain of the new species *Bacillus agaradhierens*. As described above, *Bacillus agaradhierens* is a new species of alkalophilic Bacilli, which has been disclosed by Nielsen et al. (1995) supra. The strain was formerly referred to as Bacillus AC13. Therefore, in another embodiment, the DNA construct of the invention is derived from a strain of Bacillus AC13.

The type strain of *Bacillus agaradhierens* is the strain DSM 8721, which strain has been deposited in the open collection of Deutsche Sammlung von Mikroorganismen und Zellkulturen GmbH (DSM), Mascheroder Weg 1b, DE-3300 Braunschweig, Germany.

The strain Bacillus AC13, also a representative of the new species *Bacillus agaradhierens,* has been deposited according to the Budapest Treaty on the International Recognition of the Deposit of Microorganisms for the Purposes of Patent Procedure at National Collections of Industrial and Marine Bacteria, Ltd. (NCIB), 23 St. Machar Drive, GB-Aberdeen AB2 1RY, United Kingdom, on Mar. 3, 1992 and allotted the deposit number NCIB 40482. As an International Depository Authority under the Budapest Treaty, NCIB affords permanence of the deposit in accordance with the rules and regulations of said treaty, vide in particular Rule 9. Access to the deposit will be available during the pendency of this patent application to one determined by the Commissioner of the United States Patent and Trademark Office to be entitled thereto under 37 C.F.R. Par. 1.14 and 35 U.S.C. Par. 122. Also, the above mentioned deposit fulfills the requirements of European patent applications relating to microorganisms according to Rule 28 EPC.

In a more preferred embodiment, the DNA construct of the invention is derived from the strain NCIMB 40482, or the strain DSM 8721, or mutants or variants thereof. The DNA sequence encoding the cellulytic enzyme may be isolated from these deposits by standard methods, e.g. as described in Example 1.

Further, said DNA sequence may be isolated by screening a cDNA library of a strain of *Bacillus agaradhierens,* followed by selection for clones expressing the cellulytic enzyme (e.g. as defined by their ability to degrade cellulose). The appropriate DNA sequence may then be isolated from the clone by standard procedures.

Alternatively, the DNA encoding the cellulytic enzyme may, in accordance with well-known procedures, conveniently be isolated from DNA from the source in question by use of synthetic oligonucleotide probes prepared on the basis of a DNA sequence disclosed herein. For instance, a suitable oligonucleotide probe may be prepared on the basis of the nucleotide sequences presented as SEQ ID NO:1, or any suitable fragment thereof.

Recombinant Expression Vectors

In another aspect, the invention provides a recombinant expression vector comprising the DNA construct of the invention.

The expression vector of the invention may be any expression vector that is conveniently subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the expression vector of the invention, the DNA sequence encoding the cellulytic enzyme preferably is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the cellulytic enzyme.

Thus, in the expression vector of the invention, the DNA sequence encoding the cellulytic enzyme preferably should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the cellulytic enzyme, the promoter and the terminator, respectively, and to insert them into suitable vectors are well known to persons skilled in the art (cf., for instance, Sambrook et al.(1989) supra.

The promoter may be any DNA sequence which shows transcriptional activity in the host cell of choice and may be derived from genes encoding proteins either homologous or heterologous to the host cell. Examples of suitable promoters for directing the transcription of the DNA encoding the cellulytic enzyme of the invention in bacterial host cells include the promoter of the *Bacillus stearothermophilis* maltogenic amylase gene, the *Bacillus licheniformis* alpha-amylase gene, the *Bacillus amyloliquefaciens* BAN amylase gene, the *Bacillus subtilis* alkaline protease gene, or the *Bacillus pumilus* xylanase or xylosidase gene, the phage Lambda $P_R$ or $P_L$ promoters, or the *E. coli* lac, trp or tac promoters.

Examples of suitable promoters for use in yeast host cells include promoters from yeast glycolytic genes (Hitzeman et al. (1980) J. Biol. Chem. 255:12073–12080; Alber and Kawasaki (1982) J. Mol. Appl. Gen. 1:419–434) or alcohol dehydrogenase genes (Young et al. (1982) in *Genetic Engineering of Microorganisms for Chemicals* (Hollaender et al, eds.), Plenum Press, New York), or the TPI1 (U.S. Pat. No. 4,599,311) or ADH2-4c (Russell et al. (1983) Nature 304:652–654) promoters.

Examples of suitable promoters for use in filamentous fungus host cells are, for instance, the ADH3 promoter (McKnight et al. (1985) EMBO J. 4:2093–2099) or the tpiA promoter. Examples of other useful promoters are those derived from the gene encoding *A. oryzae* TAKA amylase, *Rhizomucor miehei* aspartic proteinase, *A. niger* neutral a-amylase, *A. niger* acid stable a-amylase, *A. niger* or *A. awamori* glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters.

The expression vector of the invention may further comprise a DNA sequence enabling the vector to replicate in the host cell in question. The expression vector may also comprise a selectable marker, e.g. a gene the product of which complements a defect in the host cell, such as the gene coding for dihydrofolate reductase (DHFR) or the *Schizosaccharomyces pombe* TPI gene (described by Russell (1985) Gene 40:125–130), or one which confers resistance to a drug, e.g. ampicillin, kanamycin, tetracyclin, chloramphenicol, neomycin, hygromycin or methotrexate. For filamentous fungi, selectable markers include amdS, pyrG, argB, niaD and sC.

To direct the cellulytic enzyme into the secretory pathway of the host cells, a secretory signal sequence (also known as a leader sequence, prepro sequence or pre sequence) may be provided in the expression vector. The secretory signal sequence is joined to the DNA sequence encoding the cellulytic enzyme in the correct reading frame. Secretory signal sequences are commonly positioned 5' to the DNA sequence encoding the cellulytic enzyme. The secretory signal sequence may be that normally associated with the cellulytic enzyme or may be from a gene encoding another secreted protein.

In a preferred embodiment, the expression vector of the invention may comprise a secretory signal sequence substantially identical to the secretory signal encoding sequence of the *Bacillus licheniformis* a-amylase gene, e.g. as described in WO 86/05812.

Also, measures for amplification of the expression may be taken, e.g. by tandem amplification techniques, involving single or double crossing-over, or by multicopy techniques, e.g. as described in U.S. Pat. No. 4,959,316 or WO 91/09129. Alternatively the expression vector may include a temperature sensitive origin of replication, e.g. as described in EP 283,075.

Procedures for ligating DNA sequences encoding the cellulytic enzyme, the promoter and optionally the terminator and/or secretory signal sequence, respectively, and to insert them into suitable vectors containing the information necessary for replication, are well known to persons skilled in the art (cf., for example, Sambrook et al. (1989) supra.

Host Cells

In yet another aspect the invention provides a host cell containing the DNA construct of the invention and/or the recombinant expression vector of the invention.

The DNA construct of the invention may be either homologous or heterologous to the host in question. If homologous to the host cell, i.e. produced by the host cell in nature, it will typically be operably connected to another promoter sequence or, if applicable, another secretory signal sequence arid/or terminator sequence than in its natural environment. In this context, the term "homologous" is intended to include a cDNA sequence encoding a cellulytic enzyme native to the host organism in question. The term "heterologous" is intended to include a DNA sequence not expressed by the host cell in nature. Thus, the DNA sequence may be from another organism, or it may be a synthetic sequence.

The host cell of the invention, into which the DNA construct or the recombinant expression vector of the invention is to be introduced, may be any cell which is capable of producing the cellulytic enzyme and includes bacteria, yeast, fungi and higher eukaryotic cells.

Examples of bacterial host cells which, on cultivation, are capable of producing the cellulytic enzyme of the invention are grampositive bacteria such as strains of Bacillus, in particular a strain of *B. subtilis, B. licheniformis, B. lentus, B. brevis, B. stearothermophilus, B. alkalophilus, B. amyloliquefaciens, B. coagulans, B. circulans, B. lautus, B. megatherium, B. pumilus, B. thuringiensis* or *B. agaradhierens,* or strains of Streptomyces, in particular a strain of *S. lividans* or *S. murinus,* or gramnegative bacteria such as *Echerichia coli*. The transformation of the bacteria may be effected by protoplast transformation or by using competent cells in a manner known per se (cf. Sambrook et al. (1989) supra).

When expressing the cellulytic enzyme in bacteria such as *E. coli,* the cellulase may be retained in the cytoplasm, typically as insoluble granules (known as inclusion bodies), or may be directed to the periplasmic space by a bacterial secretion sequence. In the former case, the cells are lysed and the granules are recovered and denatured after which the cellulytic enzyme is refolded by diluting the denaturing agent. In the latter case, the cellulytic enzyme may be recovered from the periplasmic space by disrupting the cells, e.g. by sonication or osmotic shock, to release the contents of the periplasmic space and recovering the cellulytic enzyme.

Examples of suitable yeasts cells include cells of Saccharomyces spp. or Schizosaccharomyces spp., in particular strains of *Saccharomyces cerevisiae* or *Saccharomyces kluyveri*. Methods for transforming yeast cells with heterologous DNA and producing heterologous polypeptides therefrom are described, e.g. in U.S. Pat. Nos. 4,599,311, 4,931,373, 4,870,008, 5,037,743, and 4,845,075, all of which are hereby specifically incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequence encoding the cellulytic enzyme of the invention may be preceded by a signal sequence and optionally a leader sequence, e.g. as described above. Further examples of suitable yeast cells are strains of Kluyveromyces, such as *K. lactis,* Hansenula, e.g. *H. polymorpha,* or Pichia, e.g. *P. pastoris* (cf. Gleeson et al. (1986) J. Gen. Microbiol. 132:3459–3465; U.S. Pat. No. 4,882,279).

Examples of other fungal cells are cells of filamentous fungi, e.g. Aspergillus spp., Neurospora spp., Fusarium spp. or Trichoderma spp., in particular strains of *A. oryzae, A. nidulans* or *A. niger.* The use of Aspergillus spp. for the expression of proteins have been described in e.g., EP 272,277 and EP 230,023. The transformation of *F. oxysporum* may, for instance, be carried out as described by Malardier et al. (1989) Gene 78:147–156.

The transformed or transfected host cell described above is then cultured in a suitable nutrient medium under conditions permitting the expression of the cellulytic enzyme, after which the resulting cellulytic enzyme is recovered from the culture.

The medium used to culture the cells may be any conventional medium suitable for growing the host cells, such as minimal or complex media containing appropriate supplements. Suitable media are available from commercial suppliers or may be prepared according to published recipes (e.g., in catalogues of the American Type Culture Collection). The cellulytic enzyme produced by the cells may then be recovered from the culture medium by conventional procedures including separating the host cells from the medium by centrifugation or filtration, precipitating the proteinaceous components of the supernatant or filtrate by means of a salt, e.g., ammonium sulphate, purification by a variety of chromatographic procedures, e.g., ion exchange chromatography, gelfiltration chromatography, affinity chromatography, or the like, dependent on the type of cellulytic enzyme in question.

Method of Producing Cellulytic Enzymes

The present invention also relates to methods for producing a polypeptide of the present invention comprising (a) cultivating a Bacillus strain to produce a supernatant comprising the polypeptide; and (b) recovering the polypeptide.

The present invention also relates to methods for producing a polypeptide of the present invention comprising (a) cultivating a host cell under conditions conducive to expression of the polypeptide; and (b) recovering the polypeptide.

In both methods, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art (see, e.g., references for bacteria and yeast; Bennett, J. W. and LaSure, L., eds. (1991) More Gene Manipulations in Fungi, Academic Press, California). Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it is recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide. Procedures for determining cellulytic activity are known in the art and are described in the examples below.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation. The recovered polypeptide may then be further purified by a variety of chromatographic procedures, e.g., ion exchange chromatography, gel filtration chromatography, affinity chromatography, or the like.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification (Janson and Ryden, eds.), VCH Publishers, New York, 1989).

Polypeptide Preparations

In a still further aspect, the present invention relates to polypeptide compositions and preparations which are enriched in the cellulytic enzyme of the invention encoded by a DNA construct of the invention, or produced by the method of the invention.

The enzyme preparation of the invention may be one which comprises the polypeptide of the invention as the major enzymatic component, and may in particular be a mono-component enzyme preparation. Alternatively, the composition may comprise multiple enzymatic activities, such as an aminopeptidase, an amylase, a carbohydrase, a carboxypeptidase, a catalase, a cellulase, a chitinase, a cutinase, a deoxyribonuclease, an is esterase, an alpha-galactosidase, a beta-galactosidase, a glucoamylase, an alpha-glucosidase, a beta-glucosidase, a haloperoxidase, an invertase, a laccase, a lipase, a mannosidase, a mutanase, an oxidase, a pectinolytic enzyme, a peroxidase, a phytase, a polyphenoloxidase, a proteolytic enzyme, a ribonuclease, or a xylanase. The additional enzyme(s) may be producible by means of a microorganism belonging to the genus Aspergillus, preferably *Aspergillus niger, Aspergillus aculeatus, Aspergillus awamori* or *Aspergillus oryzae,* or Trichoderma, Humicola, preferably *Humicola insolens,* or Fusarium, preferably *Fusarium graminearum.*

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The enzyme preparation according to the invention may be applied in industrial processes conventionally involving the action of cellulytic enzymes. Major applications for cellulytic enzymes are found in the detergent industry, in the textile industry, in paper pulp processing industry, and in the food and feed industry.

In preferred embodiments the enzyme preparation of the invention may be used for degradation or modification of plant material, e.g. cell walls, for the treatment of fabric or textile, preferably for preventing backstaining, for biopolishing or "stone-washing" cellulosic fabric, in the treatment of paper pulp, preferably for debarking, defibration, fibre modification, enzymatic de-inking or drainage improvement.

EXAMPLES

The following examples are put forth so as to provide those of ordinary skill in the art with a complete disclosure and description of how to make and use various constructs and perform the various methods of the present invention and are not intended to limit the is scope of what the inventors regard as their invention. Unless indicated otherwise, parts are parts by weight, temperature is in degrees centigrade, and pressure is at or near atmospheric pressure. Efforts have been made to ensure accuracy with respect to numbers used (e.g., length of DNA sequences, molecular weights, amounts, particular components, etc.), but some deviations should be accounted for.

EXAMPLE 1

Materials and Methods

Cellulytic Activity. Cellulytic activity may be measured in cellulase viscosity units (CEVU), determined at pH 9.0 with carboxymethyl cellulose (CMC) as substrate.

Cellulase viscosity units are determined relatively to an enzyme standard (<1% water, kept in $N_2$ atmosphere at $-20°$ C.; arch standard at $-80°$ C.). The standard used, 17–1187, is 4400 CEVU/g under standard incubation conditions, i.e., pH 9.0, Tris Buffer 0.1 M, CMC Hercules 7 LFD substrate 33.3 g/l, 40.0° C. for 30 minutes.

Donor Organism. Bacillus AC13 NCIMB 40482 (identical to *Bacillus agaradhierens* DSM 8721) expressing the endoglucanase enzyme encoding the DNA sequence of SEQ ID NO:1.

Other Strains. *E. coli* strain: Cells of *E. coli* SJ2 (Diderichsen et al. (1990) J. Bacteriol. 172:4315–4321), which encodes alpha-acetolactate decarboxylase, an exoenzyme from *Bacillus brevis* were prepared for and transformed by electroporation using a Gene Pulser™ electroporator from BIO-RAD as described by the supplier.

*Bacillus subtilis* PL2304: This strain is the *B. subtilis* DN1885 (Diderichsen et al. (1990) supra), disrupted in the transcriptional unit of the known *Bacillus subtilis* cellulase gene, resulting in cellulase negative cells. The disruption was performed essentially as described by Hoch & Losick (1993) in *Bacillus subtilis* and other Gram-Positive Bacteria (Sonenshein, A. L., ed.), pp. 618).

Plasmids. pSJ1678: Described in WO 94/19454; pDN1981: Described by Jorgensen et al. (1990) Gene 96:37–41).

EXAMPLE 2

Cloning of *Bacillus agaradhierens* Endoglucanase Gene

Genomic DNA Preparation. The strain NCIMB 40482 (identical to *Bacillus agaradhierens* DSM 8721) was propagated in liquid medium as described in WO 94/01532. After 16 hours of incubation at 30° C. and 300 rpm, the cells were harvested, and genomic DNA was isolated by the method described by Pitcher et al. (1989) Lett. Appl. Microbiol. 8:151–156).

Genomic Library Construction. Genomic DNA was partially digested with restriction enzyme Sau3A and size-fractionated by electrophoresis on a 0.7% agarose gel. Fragments of between 2 and 7 kb in size were isolated by electrophoresis onto DEAE-cellulose paper (Dretzen et al. (1981) Anal. Biochem. 112:295–298). Isolated DNA fragments were ligated to BamHI digested, pSJ1678 plasmid DNA.

PCR Amplification. In order to obtain the endoglucanse gene as ligated to the pSJ1678 vector, the ligation mixture was used as DNA template in a PCR reaction containing 200 mM of each nucleotide (dATP, dCTP, dGTP and dTTP), 2.5 mM $MgCl_2$, Expand High Fidelity buffer, 2.0 units of Expand High Fidelity PCR system enzyme mix and 300 nM of each of the following primers: Primer 1 (#9555): 5'-TCACAGATCCTCGCGAATTGGT GCGGCCGCGTNGTNG-ARGARCAYGGNC-3' (SEQ ID NO:3). Primer 1 is a degenerated primer designed to match the amino acid sequence (Val-Val-Glu-Glu-His-Gly-Gln) (SEQ ID NO:4) of the N-terminal amino acid sequence presented in WO94/01532. The last amino acid is only presented by the first nucleotide of the codon namely C. C is the 3'-nucleotide of the primer. Furthermore, a NotI site is included at the 5'-end for cloning purposes these nucleotides are underlined. Primer 2 (#9029): 5'-CAGAGCAAGAGATTACGCGC-3' (SEQ ID-NO:5). Primer 2 corresponds to a sequence present in the pSJ1678 vector.

The PCR cycling was performed in a Hans Landgraf THERMOCYCLERÔ (Hans Landgraf, Germany), following the profile:

1×(120 seconds at 94° C.);

10×(10 seconds at 94° C.; 30 seconds at 55° C.; 240 seconds at 72° C.);

30×(10 seconds at 94° C.; 30 seconds at 55° C.; 180 seconds at 72° C.; adding 20 seconds to the keep time at 72° C. for each new cycle); and 1×(300 seconds at 72° C.).

The PCR product was gel purified by gel electrophoresis in a 0.7% agarose gel, and the relevant fragment (approx. 1.7 kb) was excised from the gel and purified using QIAquickÔ Gel extraction Kit (Qiagen, USA) according to the manufacturer's instructions. The purified DNA was eluted in 50 μl of 10 mM Tris-HCl, pH 8.5.

This DNA was used as a template for a PCR reamplification using the same is primers, mixture and cycle profile as above.

The PCR product was gel purified by gel eletrophoresis in a 0.7% agarose gel, and the relevant fragment was excised from the gel and purified using QIAquick Gel extraction Kit. The purified DNA was eluted in 50 μl of 10 mM Tris-HCl, pH 8.5.

The purified DNA was digested with NotI and HindIII, gel purified as above, and ligated to the vector pBluescriptII KS– (Stratagene, USA), also digested with NotI and HindIII, and the ligation mixture was used to transform *E. coli* SJ2.

Cells were plated on LB agar plates containing ampicillin (200 μg/ml) supplemented with X-gal (5-Bromo-4-chloro-3-indolyl alpha-D-Galactopyranoside, 50 μg/ml).

Identification and Charaterization of Positive Clones. The transformed cells were plated on LB agar plates containing ampicillin (200 μg/ml) supplemented with X-gal (5-Bromo-4-chloro-3-indolyl alpha-D-Galactopyranoside, 50 μg/ml), and incubated at 37° C. overnight. The next day white colonies were rescued by restreaking these onto fresh LB-ampicillin agar plates and incubated at 37° C. overnight. The day after, single colonies of each clone were transferred to liquid LB medium containing ampicillin (200 μg/ml), and incubated overnight at 37° C. with shaking at 250 rpm.

Plasmids were extracted from the liquid cultures using QIAgen Plasmid Purification mini kit. Five-μl samples of the plasmids are digested with NotI and HindIII. The digestions were checked by gel electrophoresis on a 0.7% agarose gel (NuSieve, FMC). The appearence of a DNA fragment of approximately 1.0 kb indicated a positive clone.

Nucleotide Sequencing the Cloned DNA Fragment. Qiagen purified plasmid DNA was sequenced with the Taq deoxy terminal cycle sequencing kit (Perkin Elmer, USA) and the primer "Reverse" or the primer "Forward": Reverse: 5'-GTTTTCCCAGTCACGAC-3' (SEQ ID NO:6), Forward: 5'-GCGGATAACAATTTCACACAGG-3' (SEQ ID NO:7).

The DNA was sequenced using an Applied Biosystems 373A automated sequencer according to the manufacturers instructions. Analysis of the sequence data is performed according to Devereux et al. (1984) Nucleic Acids Res. 12:387–395).

From this sequence new primers could be designed for performing Inverse PCR [cf. McPherson et al. (eds) in *PCR-A practical approach;* 1991 IRL Press).

Inverse PCR on Genomic DNA of Strain NCIMB 40482. Genomic DNA was isolated as described above. 2 mg of pure genomic DNA was digested with EcoRI. The EcoRI was heat inactivated at 65° C. for 20 minutes, after which a phenol:chloroform extraction of DNA was performed. DNA was finally ethanol precipitated and resuspended in 20 ml TE.

1 ml of EcoRI digested DNA was ligated with T4-DNA ligase in 100 ml reaction mixture containing T4 ligase buffer and 1 Unit T4-DNA ligase (Boehringer Mannheim, Germany). After 18 hours of ligation at 14° C., the ligase was heat inactivated at 68° C. for 10 minutes. In order to linearize the circulized genomic DNA fragments prior to Inverse PCR, the ligation mixture was supplemented with 10 U of BstEII (a BstEII site was present internally of the DNA sequence obtained above).

50 ml of the BstEII digested ligation mixture was used as template in a PCR reaction containing 200 mM of each nucleotide (dATP, dCTP, dGTP and dTTP), 2.5 mM MgCl$_2$, Expand High Fidelity buffer, 2.0 units of Expand High Fidelity PCR system enzyme mix, and 300 nM of each of the following primers:

Primer 3 (#19719): 5'-TGACCCGTACGGTCCGTGGG-3' (SEQ ID NO:8), and Primer 4

(#19720): 5'-GGCTCTTGATTTTGTGTCCACC-3' (SEQ ID NO:9).

The PCR cycling was performed in a Hans Landgraf THERMOCYCLER (Hans Landgraf, Germany), following the profile:

1×(120 seconds at 94° C.);

10×(10 seconds at 94° C.; 30 seconds at 55° C.; 240 seconds at 72° C.);

30×(10 seconds at 94° C.; 30 seconds at 55° C.; 180 seconds at 72° C. adding 20 seconds to the keep time at 72° C. for each new cycle); and 1×(300 seconds at 72° C.).

The PCR product was gel purified by gel eletrophoresis in a 0.7% agarose gel, and the relevant fragment (approx. 4–5 kb) was excised from the gel and purified using QIAquick Gel extraction Kit. The purified DNA was eluted in 50 μl of 10 mM Tris-HCl, pH 8.5.

Nucleotide Sequencing the Inverse-PCR DNA Fragment. Qiagen purified DNA was sequenced with the Taq deoxy terminal cycle sequencing kit (Perkin Elmer, USA), and the primer 1, 3 and 4 described above, using an Applied Biosystems 373A automated sequencer according to the manufacturers instructions. Analysis of the sequence data is performed according to Devereux et al. (1984) supra).

The entire nucleotide sequence corresponding to the open reading frame of the alkaline endoglucanase is presented as SEQ ID NO:1, and the derived protein sequence is presented as SEQ ID NO:2.

EXAMPLE 3

Expression of the Alkaline Endoglucanase in *Bacillus subtilis*

The nucleotide sequence in SEQ ID NO:1 was cloned by PCR for introduction in an expression plasmid pDN1981. PCR was performed as described above on 500 ng of genomic DNA, using the following two primers, containing NdeI and KpnI restriction sites for introducing the endoglucanase encoding DNA sequence to pDN1981 for expression:

Primer 5 (#20887): 5'-GTAGGCTCAGT<u>CATATG</u>TTAC ACATTGAAAGGGGAGGAGAATCATGAAAAA GATAACTACTATTTTTGTCG-3' (SEQ ID NO:10); and Primer 6 (#21318): 5'-GTACCTCGCG<u>GGTACC</u>AAGCG GCCGCTTAATTGAGTGGTTCCCACGGACCG-3' (SEQ ID NO:11).

After PCR cycling, the PCR fragment was purified, and the purified DNA was eluted in 50 μl of 10 mM Tris-HCl, pH 8.5, digested with NdeI and KpnI, purified and ligated to digested pDN1981. The ligation mixture was used to transform *B. subtilis* PL2304. Competent cells were prepared and transformed as described by Yasbin et al. (1975) J. Bacteriol. 121:296–304).

EXAMPLE 4

Isolation and Test of *Bacillus subtilis* Transformants

The transformed cells were plated on LB agar plates containing 10 mg/ml Kanamycin, 0.4% glucose, 10 mM KH2PO4 and 0.1% AZCL HE-cellulose (Megazyme, Australia), and incubated at 37° C. for 18 hours. Endoglucanase positive colonies were identified as colonies surrounded by a blue halo.

Each of the positive transformants were inoculated in 10 ml TY-medium containing 10 mg/ml Kanamycin. After 1 day of incubation at 37° C. and stirring at 250 rpm, 50 ml supernatant was removed. The endoglucanase activity was identified by adding 50 ml supernatant to holes punched in the agar of LB agar plates containing 0.1% AZCL HE-cellulose.

After 16 hours of incubation at 37° C., blue halos surrounding holes indicated expression of the endoglucanase in *Bacillus subtilis*.

EXAMPLE 5

Characterization of the Purified Enzyme

The cellulytic enzyme consists of a signal peptide (i.e. amino acid residues 1 to 26), a catalytic core domain belonging to the family 5 (1) of the Bacillus subfamily (i.e. amino acid residues 1 to 306), followed by a short linker region (i.e. amino residues 307 to 328), and finally new class of cellulose binding domain, CBD (i.e. amino acid residues 329 to 376).

The molar extinction coefficient was determined as 114,000. The molecular weight was approximately 43 kD. It was determined that the enzyme does not contain a cysteine residue, and the charged amino acids give a calculated pI of around 4.

The enzyme has a broad pH profile and very high alkaline activity, and has a temperature optima of around 60° C. The product is fully stable after one hour of incubation in an American standard detergent solution at 40° C.

The purified enzyme has a maximal activity at 60° C., 3 times higher than that observed at 40° C.

EXAMPLE 6

Expression of the Alkaline Endoglucanase in *Bacillus subtilis*

The nucleotide sequence in SEQ ID NO: 12 was cloned by PCR for introduction in an expression plasmid pDN1981.

PCR was performed as described below on 500 ng of genomic DNA, using the following two primers containing NdeI and KpnI (the KpnI site is conveniently present in the amplified sequence) restriction sites for introducing the endoglucanase encoding DNA sequence to pDN1981 for expression:

Primer 5 (#20887): 5'-GTA GGC TCA GT<u>C ATA TGT</u> TAC ACA TTG AAA GGG GAG GAG AAT CAT GAA AAA GAT AAC TAC TAT TTT TGT CG-3' (SEQ ID NO:10), and Primer 7 (#100084): 5'-CCT CGC GAG GTA CCA GCG GCC GCG TAC CAC CAA TTA AGT AT<u>G GTA C</u>-3' (SEQ ID NO: 14)

The underlined nucleotides of Primer 5 corresponds to the NdeI site, and the underlined nucleotides in the Primer 7 is part of the KpnI site present in the sequence.

Using the Expand™ Long Template PCR system (available from Boehringer Mannheim, Germany) amplification was performed using a mixture consisting of (Buffer 1 diluted 10 times) and 200 μM of each dNTP, 2.5 units of Enzyme mix (Boehringer Mannheim, Germany) and 500 pmol of each primer.

The PCR reactions was performed using a DNA Thermal Cycler (available from Landgraf, Germany). One incubation at 94° C. for 2 min followed by ten cycles of PCR performed using a cycle profile of denaturation at 94° C. for 10 seconds, annealing at 55° C. for 30 seconds, and extension at 68° C. for 4 minutes. Followed by 25 cycles of PCR performed using a cycle profile of denaturation at 94° C. for 10 seconds, annealing at 55° C. for 30 seconds, and extension at 68° C. for 3 minutes (this duration of extension is extended with 20 seconds for each of the 25 cycles).

Aliquots of 10 μl of the amplification product is analysed by electrophoresis in 0.7% agarose gels (NuSieve, FMC) with ReadyLoad 100 bp DNA ladder (GibcoBRL, Denmark) as a size marker.

After PCR cycling, the PCR fragment was purified using QIAquick PCR column Kit (Qiagen, USA) according to the manufacturer's instructions. The purified DNA was eluted in 50 μl of 10 mM Tris-HCl, pH 8.5, digested with NdeI and KpnI, and purified and ligated to digested pDN1981. The ligation mixture was used to transform *B. subtilis* PL2304.

Competent cells were prepared and transformed as described by Yasbin et al. [Yasbin R E, Wilson G A & Young F E; Transformation and transfection in lysogenic strains of *Bacillus subtilis*: evidence for selective induction of prophage in competent cells; *J Bacteriol* 1975 121 296–304].

Isolation and Test of *Bacillus subtilis* Transformants

The transformed cells were plated on LB agar plates containing 10 mg/ml Kanamycin, 0.4% glucose, 10 mM KH2PO4 and 0.1% AZCL HE-cellulose (Megazyme, Australia), and incubated at 37° C. for 18 hours. Endoglucanase positive colonies were identified as colonies surrounded by a blue halo.

Each of the positive transformants were inoculated in 10 ml TY-medium containing 10 mg/ml Kanamycin. After 1 day of incubation at 37° C. and stirring at 250 rpm, 50 ml supernatant was removed. The endoglucanase activity was identified by adding 50 ml supernatant to holes punched in the agar of LB agar plates containing 0.1% AZCL HE-cellulose.

After 16 hours of incubation at 37° C., blue halos surrounding holes indicated expression of the endoglucanase in *Bacillus subtilis*.

EXAMPLE 7

Analysis of the Cloned Sequence

The protein sequence derived from the cloned endoglucanase gene shows an endoglucanase of the following composition:

Amino acid residues 1 to 26 correspond to a signal peptide; amino acid residues 27 to 326 constitute the actual endoglucanase (homologues to other family 5 glycosyl hydrolases); amino acid residues 327 to 354 correspond to a linker; amino acid residues 355 to 400 correspond to a cellulose binding domain (as described in Example 2); amino acid residues 401 to 416 correspond to a linker; and amino acid residues 417 to 462 constitute a second cellulose binding domain (highly homologues to the first one (at amino acid residues 355 to 400)).

The molar extinction coefficient was determined as 146,370. The molecular weight was approximately 52 kD.

For the protein without the signal sequence the molar extinction coefficient was determined as 146.370. The molecular weight was approximately 49 kD.

The enzyme has no cysteine, and the charged amino acids give a calculated pI of around 4.

What is claimed is:

1. An isolated polypeptide exhibiting endoglucanase activity and having an amino acid sequence selected from the group consisting of:
   (a) an amino acid sequence comprising amino acid residues 1–400 of SEQ ID NO:2;
   (b) an amino acid sequence comprising amino acid residues 27–400 of SEQ ID NO:2; and
   (c) an amino acid sequence comprising amino acid residues 27–326 of SEQ ID NO:2.

2. The polypeptide of claim 1 having an amino acid sequence comprising amino acid residues 1–400 of SEQ ID NO:2.

3. The polypeptide of claim 1 having an amino acid sequence comprising amino acid residues 27–400 of SEQ D NO:2.

4. The polypeptide of claim 1 having an amino acid sequence comprising amino acid residues 27–326 of SEQ ID NO:2.

5. An enzyme preparation comprising a polypeptide of claim 1.

6. A method of modifying a cellulosic material, comprising contacting the material with an enzyme preparation of claim 5.

7. An isolated polypeptide exhibiting endoglucanase activity and having an amino acid sequence selected from the group consisting of:
   (a) an amino acid sequence comprising amino acid residues 1–462 of SEQ ID NO:13;
   (b) an amino acid sequence comprising amino acid residues 27–462 of SEQ ID NO:13;
   (c) an amino acid sequence comprising amino acid residues 1–400 of SEQ ID NO:113;
   (d) an amino acid sequence comprising amino acid residues 27–400 of SEQ ID NO:13;
   (e) an amino acid sequence comprising amino acid residues 1–326 of SEQ ID NO:13; and
   (f) an amino acid sequence comprising amino acid residues 27–326 of SEQ ID NO:13.

8. The polypeptide of claim 7 having an amino acid sequence comprising amino acid residues 1–462 of SEQ ID NO:13.

9. The polypeptide of claim 7 having an amino acid sequence comprising amino acid residues 27–462 of SEQ ID NO:13.

10. The polypeptide of claim 7 having an amino acid sequence comprising amino acid residues 1–400 of SEQ ID NO:13.

11. The polypeptide of claim 7 having an amino acid sequence comprising amino acid residues 27–400 of SEQ ID NO:13.

12. The polypeptide of claim 7 having an amino acid sequence comprising amino acid residues 1–326 of SEQ ID NO:13.

13. The polypeptide of claim 7 having an amino acid sequence comprising amino acid residues 27–326 of SEQ ID NO:13.

14. An enzyme preparation comprising a polypeptide of claim 7.

15. A method of modifying a cellulosic material, comprising contacting the material with an enzyme preparation of claim 14.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
(A) LENGTH: 1203 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Bacillus agaradherens
(B) STRAIN: AC13

(ix) FEATURE:
(A) NAME/KEY: CDS
(B) LOCATION:1..1203

(xi) SEQUENCE DESCRIPTION: SEQ ID NO: 1:

```
ATG AAA AAG ATA ACT ACT ATT TTT GTC GTA TTG CTT ATG ACA GTG GCG      48
Met Lys Lys Ile Thr Thr Ile Phe Val Val Leu Leu Met Thr Val Ala
 1               5                  10                  15

TTG TTC AGT ATA GGA AAC ACG ACT GCT GCT GAT AAT GAT TCA GTT GTA      96
Leu Phe Ser Ile Gly Asn Thr Thr Ala Ala Asp Asn Asp Ser Val Val
             20                  25                  30

GAA GAA CAT GGG CAA TTA AGT ATT AGT AAC GGT GAA TTA GTC AAT GAA     144
Glu Glu His Gly Gln Leu Ser Ile Ser Asn Gly Glu Leu Val Asn Glu
         35                  40                  45

CGA GGC GAA CAA GTT CAG TTA AAA GGG ATG AGT TCC CAT GGT TTG CAA     192
Arg Gly Glu Gln Val Gln Leu Lys Gly Met Ser Ser His Gly Leu Gln
     50                  55                  60

TGG TAC GGT CAA TTT GTA AAC TAT GAA AGT ATG AAA TGG CTA AGA GAT     240
Trp Tyr Gly Gln Phe Val Asn Tyr Glu Ser Met Lys Trp Leu Arg Asp
 65                  70                  75                  80

GAT TGG GGA ATA AAT GTA TTC CGA GCA GCA ATG TAT ACC TCT TCA GGA     288
Asp Trp Gly Ile Asn Val Phe Arg Ala Ala Met Tyr Thr Ser Ser Gly
                 85                  90                  95

GGA TAT ATT GAT GAT CCA TCA GTA AAG GAA AAA GTA AAA GAG GCT GTT     336
Gly Tyr Ile Asp Asp Pro Ser Val Lys Glu Lys Val Lys Glu Ala Val
            100                 105                 110

GAA GCT GCG ATA GAC CTT GAT ATA TAT GTG ATC ATT GAT TGG CAT ATC     384
Glu Ala Ala Ile Asp Leu Asp Ile Tyr Val Ile Ile Asp Trp His Ile
        115                 120                 125

CTT TCA GAC AAT GAC CCA AAT ATA TAT AAA GAA GAA GCG AAG GAT TTC     432
Leu Ser Asp Asn Asp Pro Asn Ile Tyr Lys Glu Glu Ala Lys Asp Phe
    130                 135                 140

TTT GAT GAA ATG TCA GAG TTG TAT GGA GAC TAT CCG AAT GTG ATA TAC     480
Phe Asp Glu Met Ser Glu Leu Tyr Gly Asp Tyr Pro Asn Val Ile Tyr
145                 150                 155                 160

GAA ATT GCA AAT GAA CCG AAT GGT AGT GAT GTT ACG TGG GGC AAT CAA     528
Glu Ile Ala Asn Glu Pro Asn Gly Ser Asp Val Thr Trp Gly Asn Gln
                165                 170                 175

ATA AAA CCG TAT GCA GAG GAA GTC ATT CCG ATT ATT CGT AAC AAT GAC     576
Ile Lys Pro Tyr Ala Glu Glu Val Ile Pro Ile Ile Arg Asn Asn Asp
            180                 185                 190

CCT AAT AAC ATT ATT ATT GTA GGT ACA GGT ACA TGG AGT CAG GAT GTC     624
Pro Asn Asn Ile Ile Ile Val Gly Thr Gly Thr Trp Ser Gln Asp Val
        195                 200                 205
```

| | | |
|---|---|---|
| CAT CAT GCA GCT GAT AAT CAG CTT GCA GAT CCT AAC GTC ATG TAT GCA | 672 | |
| His His Ala Ala Asp Asn Gln Leu Ala Asp Pro Asn Val Met Tyr Ala | | |
| 210           215               220 | | |
| | | |
| TTT CAT TTT TAT GCA GGG ACA CAT GGT CAA AAT TTA CGA GAC CAA GTA | 720 | |
| Phe His Phe Tyr Ala Gly Thr His Gly Gln Asn Leu Arg Asp Gln Val | | |
| 225           230               235           240 | | |
| | | |
| GAT TAT GCA TTA GAT CAA GGA GCA GCG ATA TTT GTT AGT GAA TGG GGA | 768 | |
| Asp Tyr Ala Leu Asp Gln Gly Ala Ala Ile Phe Val Ser Glu Trp Gly | | |
| 245               250               255 | | |
| | | |
| ACA AGT GCA GCT ACA GGT GAT GGT GGC GTG TTT TTA GAT GAA GCA CAA | 816 | |
| Thr Ser Ala Ala Thr Gly Asp Gly Gly Val Phe Leu Asp Glu Ala Gln | | |
| 260               265               270 | | |
| | | |
| GTG TGG ATT GAC TTT ATG GAT GAA AGA AAT TTA AGC TGG GCC AAC TGG | 864 | |
| Val Trp Ile Asp Phe Met Asp Glu Arg Asn Leu Ser Trp Ala Asn Trp | | |
| 275               280               285 | | |
| | | |
| TCT CTA ACG CAT AAA GAT GAG TCA TCT GCA GCG TTA ATG CCA GGT GCA | 912 | |
| Ser Leu Thr His Lys Asp Glu Ser Ser Ala Ala Leu Met Pro Gly Ala | | |
| 290               295               300 | | |
| | | |
| AAT CCA ACT GGT GGT TGG ACA GAG GCT GAA CTA TCT CCA TCT GGT ACA | 960 | |
| Asn Pro Thr Gly Gly Trp Thr Glu Ala Glu Leu Ser Pro Ser Gly Thr | | |
| 305           310               315           320 | | |
| | | |
| TTT GTG AGG GAA AAA ATA AGA GAA TCA GCA TCT ATT CCG CCA AGC GAT | 1008 | |
| Phe Val Arg Glu Lys Ile Arg Glu Ser Ala Ser Ile Pro Pro Ser Asp | | |
| 325               330               335 | | |
| | | |
| CCA ACA CCG CCA TCT GAT CCA GGA GAA CCG GAT CCA ACG CCC CCA AGT | 1056 | |
| Pro Thr Pro Pro Ser Asp Pro Gly Glu Pro Asp Pro Thr Pro Pro Ser | | |
| 340               345               350 | | |
| | | |
| GAT CCA GGA GAG TAT CCA GCA TGG GAT CCA AAT CAA ATT TAC ACA AAT | 1104 | |
| Asp Pro Gly Glu Tyr Pro Ala Trp Asp Pro Asn Gln Ile Tyr Thr Asn | | |
| 355               360               365 | | |
| | | |
| GAA ATT GTG TAC CAT AAC GGC CAG CTA TGG CAA GCA AAA TGG TGG ACA | 1152 | |
| Glu Ile Val Tyr His Asn Gly Gln Leu Trp Gln Ala Lys Trp Trp Thr | | |
| 370               375               380 | | |
| | | |
| CAA AAT CAA GAG CCA GGT GAC CCG TAC GGT CCG TGG GAA CCA CTC AAT | 1200 | |
| Gln Asn Gln Glu Pro Gly Asp Pro Tyr Gly Pro Trp Glu Pro Leu Asn | | |
| 385           390               395           400 | | |
| | | |
| TAA | 1203 | |

(2) INFORMATION FOR SEQ ID NO:2:

(i) SEQUENCE CHARACTERISTICS:
        (A) LENGTH: 400 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Lys Ile Thr Thr Ile Phe Val Val Leu Leu Met Thr Val Ala
1               5                   10                  15

Leu Phe Ser Ile Gly Asn Thr Thr Ala Ala Asp Asn Asp Ser Val Val
                20                  25                  30

Glu Glu His Gly Gln Leu Ser Ile Ser Asn Gly Glu Leu Val Asn Glu
            35                  40                  45

Arg Gly Glu Gln Val Gln Leu Lys Gly Met Ser His Gly Leu Gln
        50                  55                  60

Trp Tyr Gly Gln Phe Val Asn Tyr Glu Ser Met Lys Trp Leu Arg Asp
65                  70                  75                  80

Asp Trp Gly Ile Asn Val Phe Arg Ala Ala Met Tyr Thr Ser Ser Gly

```
                    85                  90                  95
Gly Tyr Ile Asp Asp Pro Ser Val Lys Glu Lys Val Lys Glu Ala Val
                100                 105                 110
Glu Ala Ala Ile Asp Leu Asp Ile Tyr Val Ile Asp Trp His Ile
            115                 120                 125
Leu Ser Asp Asn Asp Pro Asn Ile Tyr Lys Glu Ala Lys Asp Phe
130                 135                 140
Phe Asp Glu Met Ser Glu Leu Tyr Gly Asp Tyr Pro Asn Val Ile Tyr
145                 150                 155                 160
Glu Ile Ala Asn Glu Pro Asn Gly Ser Asp Val Thr Trp Gly Asn Gln
                165                 170                 175
Ile Lys Pro Tyr Ala Glu Glu Val Ile Pro Ile Ile Arg Asn Asn Asp
                180                 185                 190
Pro Asn Asn Ile Ile Ile Val Gly Thr Gly Thr Trp Ser Gln Asp Val
                195                 200                 205
His His Ala Ala Asp Asn Gln Leu Ala Asp Pro Asn Val Met Tyr Ala
210                 215                 220
Phe His Phe Tyr Ala Gly Thr His Gly Gln Asn Leu Arg Asp Gln Val
225                 230                 235                 240
Asp Tyr Ala Leu Asp Gln Gly Ala Ala Ile Phe Val Ser Glu Trp Gly
                245                 250                 255
Thr Ser Ala Ala Thr Gly Asp Gly Val Phe Leu Asp Glu Ala Gln
                260                 265                 270
Val Trp Ile Asp Phe Met Asp Glu Arg Asn Leu Ser Trp Ala Asn Trp
            275                 280                 285
Ser Leu Thr His Lys Asp Glu Ser Ser Ala Ala Leu Met Pro Gly Ala
    290                 295                 300
Asn Pro Thr Gly Gly Trp Thr Glu Ala Glu Leu Ser Pro Ser Gly Thr
305                 310                 315                 320
Phe Val Arg Glu Lys Ile Arg Glu Ser Ala Ser Ile Pro Pro Ser Asp
                325                 330                 335
Pro Thr Pro Pro Ser Asp Pro Gly Glu Pro Asp Pro Thr Pro Pro Ser
                340                 345                 350
Asp Pro Gly Glu Tyr Pro Ala Trp Asp Pro Asn Gln Ile Tyr Thr Asn
                355                 360                 365
Glu Ile Val Tyr His Asn Gly Gln Leu Trp Gln Ala Lys Trp Trp Thr
370                 375                 380
Gln Asn Gln Glu Pro Gly Asp Pro Tyr Gly Pro Trp Glu Pro Leu Asn
385                 390                 395                 400

(2) INFORMATION FOR SEQ ID NO:3:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

TCACAGATCC TCGCGAATTG GTGCGGCCGC GTNGTNGARG ARCAYGGNC           49

(2) INFORMATION FOR SEQ ID NO:4:

(i) SEQUENCE CHARACTERISTICS:
        (A) LENGTH: 7 amino acids
```

(B) TYPE: amino acid
            (D) TOPOLOGY: linear (ii) MOLECULE TYPE: protein (xi) SEQUENCE DESCRIPTION: SEQ ID NO:4:

Val Val Glu Glu His Gly Gln
            5

(2) INFORMATION FOR SEQ ID NO:5:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

CAGAGCAAGAG ATTACGCGC                                                  20

(2) INFORMATION FOR SEQ ID NO:6:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:6:

GTTTTCCCAG TCACGAC                                                     17

(2) INFORMATION FOR SEQ ID NO:7:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:7:

GCGGATAACA ATTTCACACA GG                                               22

(2) INFORMATION FOR SEQ ID NO:8:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:8:

TGACCCGTAC GGTCCGTGGG                                                  20

(2) INFORMATION FOR SEQ ID NO:9:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

```
GGCTCTTGAT TTTGTGTCCA CC                                              22
```

(2) INFORMATION FOR SEQ ID NO:10:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
GTAGGCTCAG TCATATGTTA CACATTGAAA GGGGAGGAGA ATCATGAAAA AGATAACTAC     60

TATTTTTGTC G                                                         71
```

(2) INFORMATION FOR SEQ ID NO:11:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
GTACCTCGCG GGTACCAAGC GGCCGCTTAA TTGAGTGGTT CCCACGGACC G              51
```

(2) INFORMATION FOR SEQ ID NO: 12:

(i) SEQUENCE CHARACTERISTICS:
        (A) LENGTH: 1389 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Bacillus agaradherens
        (B) STRAIN: AC13

(ix) FEATURE:
        (A) NAME/KEY: CDS
        (B) LOCATION:1..1389

(xi) SEQUENCE DESCRIPTION: SEQ ID NO: 12:

```
ATG AAA AAG ATA ACT ACT ATT TTT GTC GTA TTG CTT ATG ACA GTG GCG      48
Met Lys Lys Ile Thr Thr Ile Phe Val Val Leu Leu Met Thr Val Ala
 1               5                  10                  15

TTG TTC AGT ATA GGA AAC ACG ACT GCT GCT GAT AAT GAT TCA GTT GTA      96
Leu Phe Ser Ile Gly Asn Thr Thr Ala Ala Asp Asn Asp Ser Val Val
                20                  25                  30

GAA GAA CAT GGG CAA TTA AGT ATT AGT AAC GGT GAA TTA GTC AAT GAA     144
Glu Glu His Gly Gln Leu Ser Ile Ser Asn Gly Glu Leu Val Asn Glu
             35                  40                  45

CGA GGC GAA CAA GTT CAG TTA AAA GGG ATG AGT TCC CAT GGT TTG CAA     192
Arg Gly Glu Gln Val Gln Leu Lys Gly Met Ser Ser His Gly Leu Gln
     50                  55                  60

TGG TAC GGT CAA TTT GTA AAC TAT GAA AGT ATG AAA TGG CTA AGA GAT     240
Trp Tyr Gly Gln Phe Val Asn Tyr Glu Ser Met Lys Trp Leu Arg Asp
 65                  70                  75                  80
```

```
GAT TGG GGA ATA AAT GTA TTC CGA GCA GCA ATG TAT ACC TCT TCA GGA    288
Asp Trp Gly Ile Asn Val Phe Arg Ala Ala Met Tyr Thr Ser Ser Gly
                85                  90                  95

GGA TAT ATT GAT GAT CCA TCA GTA AAG GAA AAA GTA AAA GAG GCT GTT    336
Gly Tyr Ile Asp Asp Pro Ser Val Lys Glu Lys Val Lys Glu Ala Val
            100                 105                 110

GAA GCT GCG ATA GAC CTT GAT ATA TAT GTG ATC ATT GAT TGG CAT ATC    384
Glu Ala Ala Ile Asp Leu Asp Ile Tyr Val Ile Ile Asp Trp His Ile
                115                 120                 125

CTT TCA GAC AAT GAC CCA AAT ATA TAT AAA GAA GAA GCG AAG GAT TTC    432
Leu Ser Asp Asn Asp Pro Asn Ile Tyr Lys Glu Glu Ala Lys Asp Phe
        130                 135                 140

TTT GAT GAA ATG TCA GAG TTG TAT GGA GAC TAT CCG AAT GTG ATA TAC    480
Phe Asp Glu Met Ser Glu Leu Tyr Gly Asp Tyr Pro Asn Val Ile Tyr
145                 150                 155                 160

GAA ATT GCA AAT GAA CCG AAT GGT AGT GAT GTT ACG TGG GGC AAT CAA    528
Glu Ile Ala Asn Glu Pro Asn Gly Ser Asp Val Thr Trp Gly Asn Gln
                165                 170                 175

ATA AAA CCG TAT GCA GAG GAA GTC ATT CCG ATT ATT CGT AAC AAT GAC    576
Ile Lys Pro Tyr Ala Glu Glu Val Ile Pro Ile Ile Arg Asn Asn Asp
            180                 185                 190

CCT AAT AAC ATT ATT ATT GTA GGT ACA GGT ACA TGG AGT CAG GAT GTC    624
Pro Asn Asn Ile Ile Ile Val Gly Thr Gly Thr Trp Ser Gln Asp Val
                195                 200                 205

CAT CAT GCA GCT GAT AAT CAG CTT GCA GAT CCT AAC GTC ATG TAT GCA    672
His His Ala Ala Asp Asn Gln Leu Ala Asp Pro Asn Val Met Tyr Ala
        210                 215                 220

TTT CAT TTT TAT GCA GGG ACA CAT GGT CAA AAT TTA CGA GAC CAA GTA    720
Phe His Phe Tyr Ala Gly Thr His Gly Gln Asn Leu Arg Asp Gln Val
225                 230                 235                 240

GAT TAT GCA TTA GAT CAA GGA GCA GCG ATA TTT GTT AGT GAA TGG GGA    768
Asp Tyr Ala Leu Asp Gln Gly Ala Ala Ile Phe Val Ser Glu Trp Gly
                245                 250                 255

ACA AGT GCA GCT ACA GGT GAT GGT GGC GTG TTT TTA GAT GAA GCA CAA    816
Thr Ser Ala Ala Thr Gly Asp Gly Gly Val Phe Leu Asp Glu Ala Gln
            260                 265                 270

GTG TGG ATT GAC TTT ATG GAT GAA AGA AAT TTA AGC TGG GCC AAC TGG    864
Val Trp Ile Asp Phe Met Asp Glu Arg Asn Leu Ser Trp Ala Asn Trp
        275                 280                 285

TCT CTA ACG CAT AAA GAT GAG TCA TCT GCA GCG TTA ATG CCA GGT GCA    912
Ser Leu Thr His Lys Asp Glu Ser Ser Ala Ala Leu Met Pro Gly Ala
290                 295                 300

AAT CCA ACT GGT GGT TGG ACA GAG GCT GAA CTA TCT CCA TCT GGT ACA    960
Asn Pro Thr Gly Gly Trp Thr Glu Ala Glu Leu Ser Pro Ser Gly Thr
                305                 310                 315                 320

TTT GTG AGG GAA AAA ATA AGA GAA TCA GCA TCT ATT CCG CCA AGC GAT   1008
Phe Val Arg Glu Lys Ile Arg Glu Ser Ala Ser Ile Pro Pro Ser Asp
            325                 330                 335

CCA ACA CCG CCA TCT GAT CCA GGA GAA CCG GAT CCA ACG CCC CCA AGT   1056
Pro Thr Pro Pro Ser Asp Pro Gly Glu Pro Asp Pro Thr Pro Pro Ser
        340                 345                 350

GAT CCA GGA AAG TAT CCA GCA TGG GAT CCA AAT CAA ATT TAC ACA AAT   1104
Asp Pro Gly Lys Tyr Pro Ala Trp Asp Pro Asn Gln Ile Tyr Thr Asn
            355                 360                 365

GAA ATT GTG TAC CAT AAC GGC CAG CTA TGG CAA GCA AAA TGG TGG ACA   1152
Glu Ile Val Tyr His Asn Gly Gln Leu Trp Gln Ala Lys Trp Trp Thr
370                 375                 380

CAA AAT CAA GAG CCA GGT GAC CCG TAC GGT CCG TGG GAA CCA CTC AAA   1200
Gln Asn Gln Glu Pro Gly Asp Pro Tyr Gly Pro Trp Glu Pro Leu Lys
385                 390                 395                 400
```

```
TCT GAT CCA GAT TCA GGA GAA CCG GAT CCA ACG CCC CCA AGT GAT CCA      1248
Ser Asp Pro Asp Ser Gly Glu Pro Asp Pro Thr Pro Pro Ser Asp Pro
                    405                 410                 415

GGA GAA TAT CCA GCA TGG GAC CCA ACG CAA ATT TAC ACA GAT GAA ATT      1296
Gly Glu Tyr Pro Ala Trp Asp Pro Thr Gln Ile Tyr Thr Asp Glu Ile
            420                 425                 430

GTG TAC CAT AAC GGC CAG CTA TGG CAA GCC AAA TGG TGG ACA CAA AAT      1344
Val Tyr His Asn Gly Gln Leu Trp Gln Ala Lys Trp Trp Thr Gln Asn
                435                 440                 445

CAA GAG CCA GGT GAC CCA TAC GGT CCG TGG GAA CCA CTC AAT TAA          1389
Gln Glu Pro Gly Asp Pro Tyr Gly Pro Trp Glu Pro Leu Asn *
        450                 455                 460

(2) INFORMATION FOR SEQ ID NO: 13:

(i) SEQUENCE CHARACTERISTICS:
        (A) LENGTH: 462 amino acids
        (B) TYPE: amino acid
        (D) TOPOLOGY: linear (ii) MOLECULE TYPE: protein (xi) SEQUENCE DESCRIPTION: SEQ ID NO: 13:

Met Lys Lys Ile Thr Thr Ile Phe Val Val Leu Leu Met Thr Val Ala
 1               5                  10                  15

Leu Phe Ser Ile Gly Asn Thr Thr Ala Ala Asp Asn Asp Ser Val Val
                20                  25                  30

Glu Glu His Gly Gln Leu Ser Ile Ser Asn Gly Glu Leu Val Asn Glu
            35                  40                  45

Arg Gly Glu Gln Val Gln Leu Lys Gly Met Ser His Gly Leu Gln
     50                  55                  60

Trp Tyr Gly Gln Phe Val Asn Tyr Glu Ser Met Lys Trp Leu Arg Asp
 65                  70                  75                  80

Asp Trp Gly Ile Asn Val Phe Arg Ala Ala Met Tyr Thr Ser Ser Gly
                 85                  90                  95

Gly Tyr Ile Asp Asp Pro Ser Val Lys Glu Lys Val Lys Glu Ala Val
            100                 105                 110

Glu Ala Ala Ile Asp Leu Asp Ile Tyr Val Ile Ile Asp Trp His Ile
        115                 120                 125

Leu Ser Asp Asn Asp Pro Asn Ile Tyr Lys Glu Glu Ala Lys Asp Phe
130                 135                 140

Phe Asp Glu Met Ser Glu Leu Tyr Gly Asp Tyr Pro Asn Val Ile Tyr
145                 150                 155                 160

Glu Ile Ala Asn Glu Pro Asn Gly Ser Asp Val Thr Trp Gly Asn Gln
                165                 170                 175

Ile Lys Pro Tyr Ala Glu Glu Val Ile Pro Ile Ile Arg Asn Asn Asp
            180                 185                 190

Pro Asn Asn Ile Ile Ile Val Gly Thr Gly Thr Trp Ser Gln Asp Val
        195                 200                 205

His His Ala Ala Asp Asn Gln Leu Ala Asp Pro Asn Val Met Tyr Ala
210                 215                 220

Phe His Phe Tyr Ala Gly Thr His Gly Gln Asn Leu Arg Asp Gln Val
225                 230                 235                 240

Asp Tyr Ala Leu Asp Gln Gly Ala Ala Ile Phe Val Ser Glu Trp Gly
                245                 250                 255

Thr Ser Ala Ala Thr Gly Asp Gly Gly Val Phe Leu Asp Glu Ala Gln
            260                 265                 270
```

```
Val Trp Ile Asp Phe Met Asp Glu Arg Asn Leu Ser Trp Ala Asn Trp
        275                 280                 285

Ser Leu Thr His Lys Asp Glu Ser Ser Ala Ala Leu Met Pro Gly Ala
    290                 295                 300

Asn Pro Thr Gly Gly Trp Thr Glu Ala Glu Leu Ser Pro Ser Gly Thr
305                 310                 315                 320

Phe Val Arg Glu Lys Ile Arg Glu Ser Ala Ser Ile Pro Pro Ser Asp
                325                 330                 335

Pro Thr Pro Pro Ser Asp Pro Gly Glu Pro Asp Pro Thr Pro Pro Ser
            340                 345                 350

Asp Pro Gly Lys Tyr Pro Ala Trp Asp Pro Asn Gln Ile Tyr Thr Asn
            355                 360                 365

Glu Ile Val Tyr His Asn Gly Gln Leu Trp Gln Ala Lys Trp Trp Thr
    370                 375                 380

Gln Asn Gln Glu Pro Gly Asp Pro Tyr Gly Pro Trp Glu Pro Leu Lys
385                 390                 395                 400

Ser Asp Pro Asp Ser Gly Glu Pro Asp Pro Thr Pro Pro Ser Asp Pro
            405                 410                 415

Gly Glu Tyr Pro Ala Trp Asp Pro Thr Gln Ile Tyr Thr Asp Glu Ile
            420                 425                 430

Val Tyr His Asn Gly Gln Leu Trp Gln Ala Lys Trp Trp Thr Gln Asn
        435                 440                 445

Gln Glu Pro Gly Asp Pro Tyr Gly Pro Trp Glu Pro Leu Asn
    450                 455                 460

(2) INFORMATION FOR SEQ ID NO: 14:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

CCTCGCGAGG TACCAGCGGC CGCGTACCAC CAATTAAGTA TGGTAC                            46
```